US00PP07773P

United States Patent [19]

Zampini

[11] Patent Number: Plant 7,773

[45] Date of Patent: Jan. 21, 1992

[54] DWARF FLOWERING CRAB APPLE TREE NAMED GUINZAM

[75] Inventor: James W. Zampini, 5052 S. Ridge Rd., Perry, Ohio 44081-0122

[73] Assignee: James W. Zampini, Perry, Ohio

[21] Appl. No.: 595,373

[22] Filed: Oct. 10, 1990

[51] Int. Cl.[5] ..... A01H 5/00
[52] U.S. Cl. ..... Plt./34
[58] Field of Search ..... Plt./34

*Primary Examiner*—James R. Feyrer
*Attorney, Agent, or Firm*—Burns, Doane, Swecker & Mathis

[57] ABSTRACT

A new and distinct variety of dwarf flowering crab apple tree named Guinzam is provided. The new variety can be readily distinguished from the Sargent crab apple tree (nonpatented in the United States). For instance, the new variety forms attractive dark pink buds which open into blossoms which simultaneously range in color from pure white to pink, generally forms stronger lateral branches having a larger diameter, and generally forms larger leaves and fruit. The new variety is particularly well suited for growing as attractive ornamentation in the landscape.

3 Drawing Sheets

SUMMARY OF THE INVENTION

The new and distinct variety Malus crab apple tree was discovered during 1974 as a seedling of unknown parentage while growing in a cultivated area tended by man. More specifically, the new variety was discovered while growing among trees of the Sargent crab apple (*Malus sargentii*) being grown on the Champion Farm of Lake County Nursery, Inc. located at Perry, Ohio in zone 6a. The seed parent of the new variety is believed to *Malus sargentii* and the pollen parent is unknown.

My attention was initially attracted to a single plant of the new variety since it was found to exhibit a combination of characteristics which differ significantly from those of the Sargent crab apple tree. Had I not discovered and preserved this new tree it would have been lost to mankind.

It has been found that the new and distinct flowering crab apple tree of the present invention exhibits the following combination of characteristics:

(a) exhibits a dwarf, generally round and broad growth habit,
(b) forms lateral branches which are somewhat descending with slightly upwardly arching tips,
(c) forms a profusion of attractive dark pink buds which open into blossoms which simultaneously range in coloration from pure white to pink,
(d) forms lateral branches which tend to be stronger and of a larger diameter than those of *Malus sargentii*,
(e) forms larger leaves than *Malus sargentii*, and
(f) forms larger fruit than *Malus sargentii*.

Trees of the new variety have been asexually reproduced by budding onto *Malus domestica* understocks. The characteristics of the new variety have been found to be strictly transmissible by such asexual propagation from one generation to another.

The new variety has been named the Guinzam variety. Also, trees of the new variety are being marketed by Lake County Nursery, Inc. of Perry, Ohio, under the Guinevere trademark.

BRIEF DESCRIPTION OF THE PHOTOGRAPHS

The accompanying photographs show as nearly true as it is reasonably possible to make the same in color illustrations of this character, typical specimens of the tree and plant parts of the new variety. The specimens depicted were grown at Perry, Ohio.

FIG. 1 illustrates a five year old tree of the new variety during the spring while blossoms are present. This particular specimen utilized a vertical rod support to encourage upright leader growth. The sturdy lateral branches are apparent which are somewhat descending with slightly upwardly arching tips.

Figure 1:
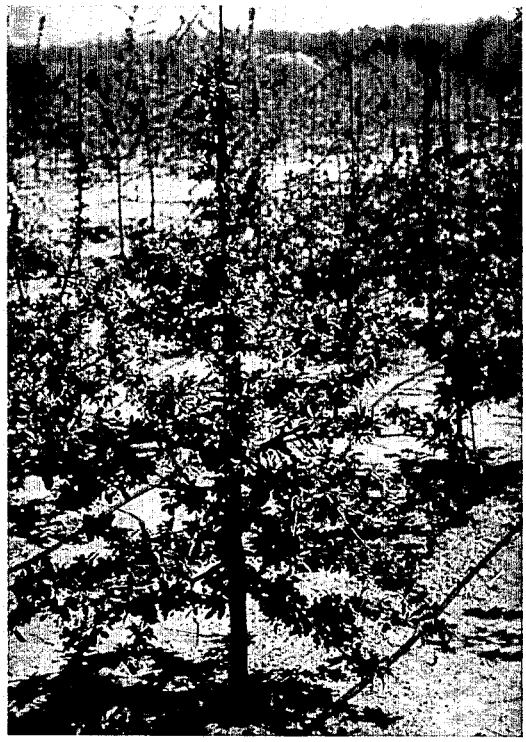
Figure 2:
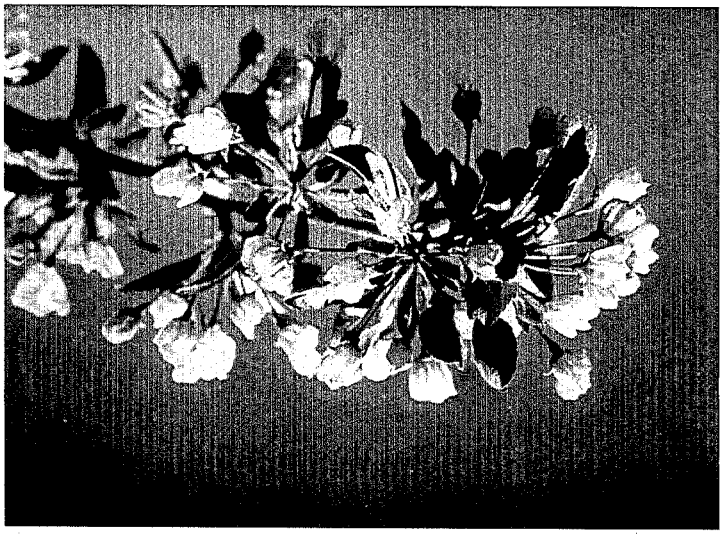
FIG. 2 illustrates the tip of a flowering branch wherein a profusion of attractive flowers is apparent which simultaneously range in color from pure white to pink. It will be noted that the tip of otherwise somewhat descending branch begins to arch slightly upwards.
Figure 3:
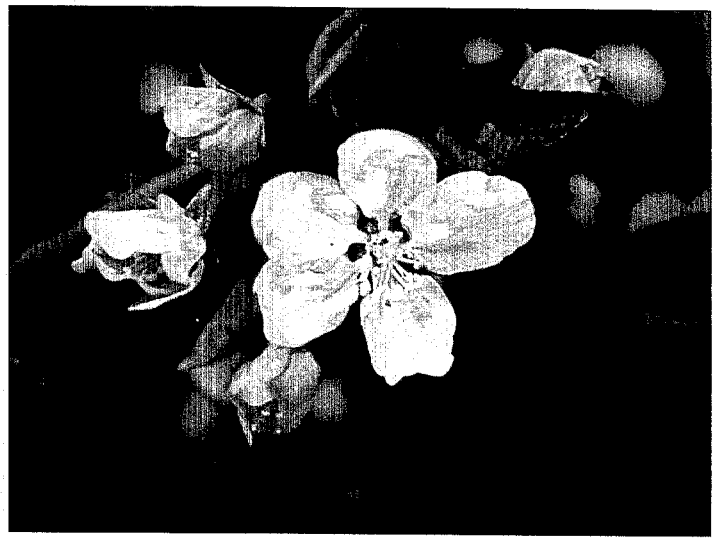
FIG. 3 illustrates a close-up view of several blossoms in various stages of opening together with some representative somewhat immature leaves.
Figure 4:
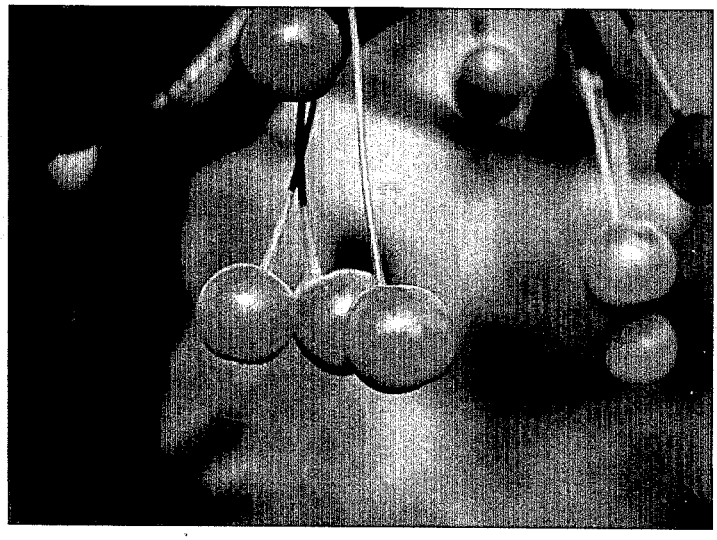
FIG. 4 illustrates representative specimens of the attractive bright red fruit of the new variety while present on the tree.
Figure 5:
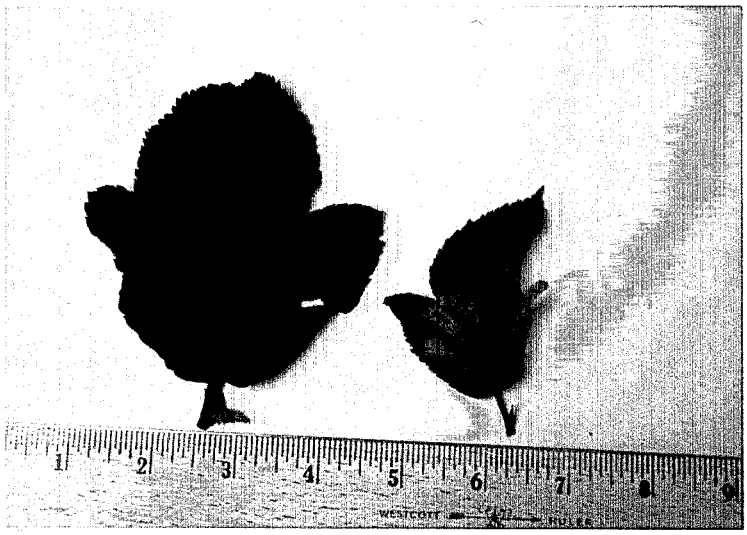

FIG. 5 illustrates for comparative purposes a representative three-lobed leaf of the new variety on the left and representative three-lobed leaf of the Sargent crab apple tree on the right. The photograph was made during late September and some initial darking of the coloration is attributable to the fall environment. The disparity in leaf sizes is apparent.

Figure 6:
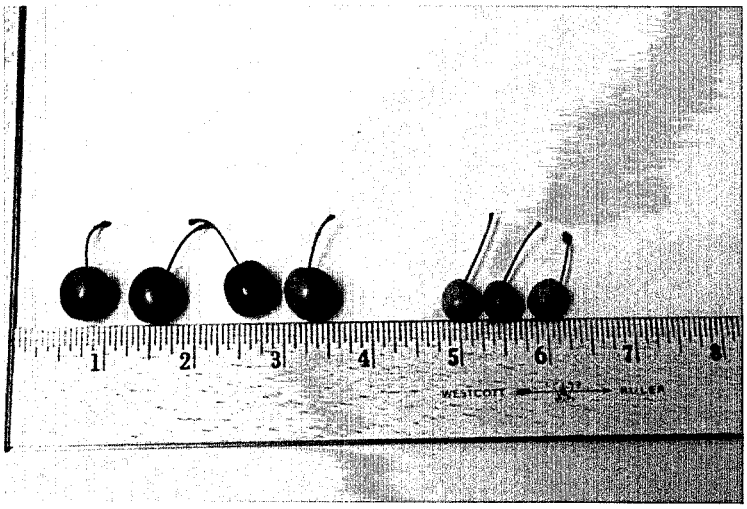

FIG. 6 illustrates four representative fruits of the new variety on the left and three representative fruits of the Sargent Crab apple tree on the right. The disparity in fruit sizes is apparent.

DETAILED DESCRIPTION

The chart used in the identification of colors is that of The Royal Horticultural Society (R.H.S. Colour Chart). Other references to color are to be accorded their ordinary dictionary significance. The descriptions are based upon trees grown at Perry, Ohio.

The original tree of the new variety exhibits a genetically controlled dwarf growth habit and presently is approximately 4 feet tall, approximately 3 feet wide and has a caliper of approximately 2½ inches at grade. Accordingly, the new variety exhibits a somewhat round and broad growth habit. When grown on its own roots, the tree is expected to reach a height of approximately 10 feet and a width of approximately 10 feet at full maturity.

The new variety has been found to exhibit lateral branches which are somewhat descending (i.e., they are pendulous). Such lateral branches also tend to be stronger and of a larger diameter than those of *Malus sargentii.* The lateral branches commonly have slightly upwardly arching tips as illustrated.

The blossom appearance of the new variety can be readily distinguished from that of the Sargent crab apple tree which is known to produce red buds which open into white blossoms. On the contrary, the present variety forms in profusion attractive dark pink buds which open into blossoms which simultaneously range in coloration from pure white to pink. The dark pink of the buds generally corresponds to that of Red Group 54A, and when open, the blossoms have been found commonly to simultaneously range in coloration from the pure white of White Group 155D through various shades of pink generally corresponding to Red Group 54A to 54D, 55A to 55D, and 56A to 56D. No blossom fragrance has been observed to date.

The configuration of the flowers is generally typical of the genus, and in particular of that of the Sargent crab apple tree. The flowers of the new variety are single and extremely numerous. Blooming commonly occurs from mid-April to mid-May at Perry, Ohio. Such flowers commonly are borne in 5 umbellate clusters on slender pedicels having a length of approximately ¾ to 1 inch which arise from fruiting spurs having a length of approximately ½ to 1 inch. The flowers commonly average approximately 1 inch at the broadest point when fully expanded. The corolla consists of 5 broadly spatulate petals which narrow abruptly to slender claws of approximately ⅛ inch in length. The slender and acute calyx lobes are reflexed.

The vegetative and reproductive parts of the variety are in most respects typical of the genus, and in particular of that of the Sargent crab apple tree. The leaves are usually three-lobed, alternate, simple, ovate and serrated and tend to be substantially larger than those of the Sargent crab apple tree as illustrated. The leaf coloration during mid-season commonly approximates that of Green Group 137A on the upper surface and tends to be somewhat paler on the under surface. The leaves have a generally rounded base and commonly end in an acuminate tip. The leaf margins are sharply serrated. When initially formed the light green leaf blades are pubescent and change to a nearly glabrous dark green with maturity. The leaves of vegetative shoots commonly reach a length of approximately 4 to 5 inches and include a maroon-colored petiole commonly measuring approximately 1 inch in length. The leaves of fruiting shoots tend to be smaller in size and variable in all dimensions. The fruiting spurs average approximately ½ to 1 inch in length. The immature twigs are maroon and villous with small orange lenticels which persist with age. Two-year old twigs tend to be a medium chocolate brown in coloration. Winter buds are medium chocolate brown in coloration and generally are glabrous except for some densely white villous margins of the bud scales.

The fruit of the new variety undergoes the usual color changes. The immature fruit of the new variety initially is bright green and develops a red blush. It will eventually completely turn bright red (as illustrated) before it ripens to a deep maroon coloration by late November when it begins to fall from the tree. The fruit is a small globose pome containing two single-seeded locules. Such fruit averages approximately ½ inch in diameter. As illustrated, the fruit of the new variety tends to be substantially larger than that of the Sargent crab apple tree which forms fruit about the size of the pea. Upon maturity, the fruit acquires a fait waxy bloom and the calyx is abscising.

I claim:

1. A new and distinct variety of flowering crab apple tree which exhibits the following combination of characteristics:

(a) exhibits a dwarf, generally round and broad growth habit,
(b) forms lateral branches which are somewhat descending with slightly upwardly arching tips,
(c) forms a profusion of attractive dark pink buds which open into blossoms which simultaneously range in coloration form pure white to pink,
(d) forms lateral branches which tend to be stronger and of a larger diameter than those of *Malus sargentii,*
(e) forms larger leaves than *Malus sargentii,* and
(f) forms larger fruit than *Malus sargentii;* substantially as herein shown and described.

* * * * *